United States Patent [19]

DeFrossez et al.

[11] Patent Number: 5,034,217
[45] Date of Patent: Jul. 23, 1991

[54] COSMETIC MAKEUP COMPOSITIONS CONTAINING CROSSLINKED POLY β-ALANINE MICROSPHERES IMPREGNATED WITH POLYHYDRIC ALCOHOL

[75] Inventors: Béatrice DeFrossez; Rose-Marie Handjani-Vila, both of Paris; Claudine Lapoiriere, Le Perreux; Claude Mahieu, Paris; Christos Papantoniou, Montmorency; Jean-Claude Ser, Chevilly Larue, all of France

[73] Assignee: Societe Anonyme dite: "L'Oreal", Paris, France

[21] Appl. No.: 342,055

[22] Filed: Apr. 24, 1989

[30] Foreign Application Priority Data

Apr. 25, 1988 [FR] France ................................. 8805447

[51] Int. Cl.$^5$ ...................... A61K 7/025; A61K 9/14

[52] U.S. Cl. ....................................... 424/64; 424/63; 424/489; 424/501; 424/502; 428/402; 428/402.2; 514/951

[58] Field of Search ................... 424/64, 63, 501, 502, 424/489; 428/402.2, 402

[56] References Cited

U.S. PATENT DOCUMENTS

| | | | |
|---|---|---|---|
| 4,590,068 | 5/1986 | Berthet et al. | 428/402 |
| 4,690,825 | 9/1987 | Won | 424/501 |
| 4,724,240 | 2/1988 | Abrutyn | 424/64 |
| 4,734,286 | 3/1988 | Mahieu et at. | 428/402 |

*Primary Examiner*—Thurman Page
*Assistant Examiner*—James M. Spear
*Attorney, Agent, or Firm*—Cushman, Darby & Cushman

[57] ABSTRACT

An anhydrous cosmetic makeup composition for the lips and skin contains crosslinked poly β-alanine microspheres impregnated with a polyhydric alcohol.

8 Claims, No Drawings

COSMETIC MAKEUP COMPOSITIONS CONTAINING CROSSLINKED POLY β-ALANINE MICROSPHERES IMPREGNATED WITH POLYHYDRIC ALCOHOL

The present invention relates to a cosmetic makeup composition for the lips and skin, such as eye makeup, cheek makeup or rouge, a complexion base or foundation or lip rouge.

More particularly, the present invention relates to cosmetic makeup products exhibiting excellent emollient characteristics which avoid dryness of the skin and improve its suppleness.

These emollient properties are generally obtained in a cosmetic by employing humectant substances which cause a rehydration of the skin by atmospheric water which these substances capture, thereby acting as a water transfer means.

This action of the humectant agents is known under the English expression "moisturizing".

The humectant substances which impart to the skin such emollient properties are essentially polyhydric alcohols and, principally, glycerol, ethylene glycol, propylene glycol and sorbitol.

These humectant substances are generally added to cosmetic compositions such as creams, and, in particular, oil-in-water type creams, for a dual purpose. On the one hand, they impart to the skin emollient properties, that is to say, they render the skin more soft and more supple, and, on the other hand, they regulate the humidity exchange between the product and the air in such a way as to avoid any tendency of the composition to dry out.

In practice, such humectant agents cannot generally be employed with the degree of efficacy desired in that they are soluble in compositions containing a certain amount of water.

Tests which have been carried out with the view of incorporating such humectant agents in anhydrous compositions, such as glycerol, have also failed to provide satisfactory results since glycerol is generally not miscible with the fatty substances employed in these compositions and it has a tendency, over time, to migrate out of the composition.

As a result of various studies in this field, the present invention provides a very satisfactory solution in that it provides an anhydrous makeup composition exhibiting good emollient action on the skin, the said composition containing porous microspheres impregnated with a polyhydric alcohol, such as, for example, glycerol.

The studies carried out have, in effect, shown that the anhydrous makeup compositions according to the invention, containing these microspheres, are particularly storage stable and confer, on application to the skin, excellent emollient properties which until the present were unattainable.

The present invention thus relates to, as a new industrial product, an anhydrous and storage stable cosmetic makeup composition, exhibiting good emollient action on the skin, this composition containing, in admixture with conventional facial makeup ingredients, a sufficient amount of crosslinked poly β-alanine microspheres impregnated with a polyhydric alcohol.

According to the invention, the polyhydric alcohol can be a compound having 2-8 carbon atoms and 2-6 hydroxy functions.

Representative polyhydric alcohols include ethylene glycol, glycerol, 1,2-propanediol, diglycerine, erythritol, arabitol, adonitol, sorbitol and dulcitol.

The polyhydric alcohol can also be a polyether alcohol having an average molecular weight between 150 and 600 such as, for instance, polyethylene Glycol 300 and Polyglycerine 500. Polyethylene Glycol 300 has a molecular weight range of 285 to 315, a viscosity of 5.8 centistokes at 100° C. and is completely soluble in water at 20° C. Anhydrous Polyglycerine 500 has an average molecular weight of 480 estimated from hydroxyl value and a viscosity of 49 poise at 30° C.

Crosslinked poly β-alanine is a known polymer, the preparation of which has been described in French Patent No. 83.11609 (2.530.250).

In accordance with this French patent, water-soluble poly β-alanine is initially prepared by polymerization of acrylamide. In a second stage, the resulting aqueous solution of poly β-alanine is crosslinked, in suspension in an organic solvent with a crosslinking agent such as, principally, glutaraldehyde.

The resulting microspheres of crosslinked poly β-alanine are then submitted to a sifting operation so as to obtain spheres having a good size homogeneity.

In accordance with this process, the microspheres are formed during the crosslinking stage and their size depends essentially on the nature and amount of the suspension agent employed.

The crosslinked poly β-alanine microspheres can also be obtained in accordance with another process which is disclosed in French patent application No. 87.17573 (non-published), this process providing microspheres having a very low size dispersity which avoids the above-mentioned sifting operation.

This latter process consists essentially in:

(a) polymerizing acrylamide in a tert.butanol/toluene solvent mixture, in the presence of a polymerization initiator and with an octadecene/maleic anhydride copolymer as the suspension agent, (b) submitting the resulting suspension of poly β-alanine microspheres to a crosslinking operation using a dialdehyde as the crosslinking agent, such as glutaraldehyde, and (c) isolating the resulting crosslinked poly β-alanine microspheres.

The low size dispersity of the crosslinked poly β-alanine microspheres is due essentially to the nature and amount of the mixed solvent employed during the polymerization of acrylamide.

Preferably, the tert.butanol/toluene solvent mixture is employed in ratios between 1:24 and 10:1 and preferably between 1:6 and 6:1.

The polymerization initiator is preferably sodium or potassium tert.butylate, employed in an amount of about 0.1 to about 2 moles/% with respect to the acrylamide.

The polymerization temperature is in the order of 60° C. to about 100° C. but preferably about 80° C.

This latter process is quite particularly advantageous since it provides, with a good reproducibility, microspheres of crosslinked poly β-alanine have a very low size dispersity.

The microspheres obtained can, if necessary, be submitted to a reduction reaction, for example, with sodium borohydride or any other similar reducing agent, so as to reduce any free aldehyde functions which exist.

For the makeup compositions according to the invention, there are preferably employed crosslinked poly β-alanine microspheres having an average diameter between 0.1 and 7 μm.

The impregnation of the crosslinked poly β-alanine microspheres with a polyhydric alcohol can be carried out following several processes. For example, the crosslinked poly β-alanine microspheres are contacted with a polyhydric alcohol in a container fitted with a powerful agitator. The initial pastey mixture progressively takes the form of a gel and then is disaggregated until there is obtained powder having a homogeneous appearance.

It is also possible to impregnate crosslinked poly β-alanine microspheres containing water with a polyhydric alcohol, the water then being removed by a classic drying operation, such as lyophilization, drying under a vacuum, etc. However, these procedures are described simply as exemplifications and have no limiting character.

In accordance with the present invention, the crosslinked poly β-alanine microspheres are generally impregnated between 10 and 600 percent by weight of the polyhydric alcohol.

The percentage of crosslinked poly β-alanine microspheres impregnated with polyhydric alcohol in the cosmetic makeup compositions, is generally between 0.1 and 60%, but preferably between 0.5 and 40% by weight relative to the total weight of the composition.

It goes without saying that the percentage selected will depend, however, on the effect sought and the amount of impregnation of the microspheres.

As indicated above the cosmetic makeup compositions according to the invention can be provided in the form of an eye shadow, cheek rouge, makeup foundation, lip rouge, free powder or even in the form of a compact powder.

When the compositions according to the invention are in the form of an eye shadow, check rouge or makeup foundation, they can be provided either in the form of a compacted powder or not, or in the form of a product containing fatty bodies and optionally an organic solvent.

When the compositions are provided in the form of a powder, compacted or not, they generally comprise:
from 0.1 to 60% of crosslinked poly β-alanine microspheres impregnated with polyhydric alcohol,
from 0 to 20% of a fatty body,
from 1 to 70% of a colored pigment, and
from 5 to 90% of a mineral or organic charge or filler, such as talc, starch and the like.

When the compositions are provided in the form of a fatty product, they generally comprise:
from 0.1 to 60% of crosslinked poly β-alanine microspheres impregnated with polyhydric alcohol,
from 5 to 98 % of a fatty body,
from 0 to 80% of a solvent, and
from 1 to 30% of a colored pigment.

In accordance with this latter form, the compositions can also contain mineral or organic charges, such as those mentioned above.

When the compositions are provided in the form of a lip rouge, colored or not, they generally comprise:
from 0.1 to 60% of crosslinked poly β-alanine microspheres impregnated with polyhydric alcohol,
from 20 to 95% of a fatty body,
from 0.2 to 10% of a mineral or organic charge, and
from 0 to 25% of a colored pigment, but preferably from 0 to 20%.

In accordance with these various forms of the composition, the fatty body is at least an oil or a mixture of at least one oil and at least one wax.

Representative oils usefully employed in the compositions according to the present invention include particularly:

mineral oils, such as paraffin oil, petrolatum oil and mineral oils having a boiling point between 310° and 410° C., oils of animal origin, such as perhydrosqualene, vegetable oils, such as sweet almond oil, calophyllum oil, palm oil, avocado oil, jojoba oil, olive oil, ricin oil, and cereal germ oils such as wheat germ oil, silicone oils, such as dimethylpolysiloxane, synthetic esters, such as Purcellin oil, butyl myristate, isopropyl myristate, cetyl myristate, isopropyl palmitate, butyl stearate, hexadecyl stearate, isopropyl stearate, octyl stearate, isocetyl stearate, decyl stearate, hexyl laurate, propylene glycol di-caprylate and di-isopropyl adipate, organic alcohols, such as oleic alcohol, linoleic alcohol, linolenic alcohol, isostearyl alcohol and octyl dodecanol, esters derived from lanolic acid, such as isopropyl lanolate and isocetyl lanolate.

Other oils include: acetylglycerides, octanoates and decanoates of alcohols and polyalcohols such as those of glycol and glycerol, ricinoleates of alcohols and polyalcohols such as that of cetyl.

Representative waxes usefully employed in the composition according to the invention include:

mineral waxes, such as microcrystalline waxes, paraffin and petrolatum, fossil waxes, such as ozokerite, and montan wax, waxes of animal origin, such as beeswax, spermaceti, lanolin wax, lanolin derivatives such as those from lanolin alcohols, hydrogenated lanolin, hydroxylated lanolin, acetylated lanolin, fatty acids of lanolin and the alcohol of acetylated lanolin, waxes of vegetable origin, such as candellila wax, carnanba wax, Japan wax and cocoa butter, hydrogenated oils solid at 25° C., such as hydrogenated ricin oil, hydrogenated palm oil, hydrogenated tallow and hydrogenated cocoa oil, synthetic waxes, such as polyethylene wax, and copolymerized polyethylene waxes, fatty esters solid at 25° C., such as propylene glycol monomyristate and myristyl myristate, and silicone waxes, such as methyloctadecaneoxypolysiloxane and poly (dimethylsiloxy) stearoxysiloxane.

Other waxes also include: cetyl alcohol, stearyl alcohol, mono-, di- and triglycerides solid at 25° C., stearic monoethanolamide, colophane and its derivatives, such as the abietates of glycol and glycerol, sucro glycerides and the oleates, myristates, lanolates, stearates and dihydroxy stearates of calcium, magnesium, zinc and aluminum.

Representative solvents usefully employed in the compositions provided under anhydrous fatty form, include, particularly: isoparaffins, cyclic or linear silicones having a boiling point lower than 200° C., chlorinated solvents and the like.

Representative colored pigments include carbon black or black iron oxide, chrome oxides, yellow and red iron oxide, ultramarines (aluminosilicate polysulfides), manganese pyrophosphate, ferric blue, titanium dioxide and finally certain metallic powders, such as those of silver or aluminum. The pigments are most often employed in admixture with nacreous agents such as bismuth oxychloride, mica-titanium, guanine crystals and certain organic dyes such as carmine and organic lakes.

These lakes which are currently employed to impart to the lips and skin a makeup effect, are salts of calcium, barium, aluminum or zirconium, acid dyes such as halogeno-acid dyes, azoic dyes, and anthraquinonic dyes.

Representative lakes include, in particular, those known under the names D and C Red 21, D and C orange 5, D and C Red 27, D and C Orange 10, D and C Red 3, D and C Red 7, D and C Red 2, D and C Red 4, D and C Red 8, D and C Red 33, D and C Yellow 5, D and C Yellow 6, D and C Green 5, D and C Yellow 10, D and C Green 3, D and C Blue 1, D and C Blue 2, D and C Violet 1, and the like.

The cosmetic makeup composition according to the present invention can also contain antioxidant agents such as the propyl, octyl and dodecyl esters of gallic acid, butylhydroxytoluene, and butyl hydroxyanisole, as well as perfumes and preservatives such as methyl or propyl parahydroxybenzoate.

The following examples are given as an illustration of the present invention without any limiting character and include an example of the preparation of crosslinked poly β-alanine microcrystals, examples of impregnation by a polyhydric alcohol and several examples of anhydrous cosmetic makeup compositions. Preparation Of Crosslinked Poly β-Alanine Microspheres Impregnated With A Lower Polyhydric Alcohol A—Preparation of Poly β-alanine Into a 3 liter reactor fitted with a type A "Ancre" stirrer having a diameter of 90 mm, a nitrogen lead-in tube, an addition funnel and a top fractionation column there are introduced 1125 g of toluene, 444 g of tert-.butanol and 0.75 g of octadecene-maleic anhydride copolymer (sold under the trade name "PA-18" by Gulf).

After heating this mixture at 70° C., 150 g of acrylamide are added. The temperature is raised to 100° C. and 90 ml of a water/toluene/tert.butanol azeotropic mixture are distilled. At the end of the distillation, the reaction mixture is cooled to 80° C., and the speed of stirring is adjusted to 600 rpm.

There is then added, over a 10 minute period, a solution of 3.36 g of potassium tert. butylate in 62 g of tert. butanol. The addition funnel is rinsed with 75 g of toluene. After stirring for 5 hours at 80° C., the reaction mixture is permitted to return to ambient temperature. There are then slowly added to the reaction mixture 11.25 ml of concentrated HCl.

B—Preparation of Crosslinked Poly β-alanine

To the suspension of poly β-alanine microspheres thus obtained, 150 ml of water are added with vigorous stirring (600 rpm) at a temperature of 50° C. Then, over a 15 minute period, 18 g of a 25% aqueous solution of glutaraldehyde are added. The suspension is permitted to return to ambient temperature. After decanting, the supernatant solvents are removed and the microspheres are washed twice with 500 ml of ethanol. Draining after each washing is carried out by centrifugation (3500 rpm). A washing with 15 liters of water is then carried out continuously. The water is then removed until a final mixture volume of 600 ml is obtained. The swollen polymer is finally dried by lyophilization and there are obtained 132 g of white powder constituted by microspheres whose average diameter of 4.05 ±2.02 μm is determined by image analysis technique on a "QUANTIMET 900" device of Cambridge Instruments Co.

C—Reduction of Residual Aldehyde Functions of The Crosslinked Poly β-alanine

To 150 g of crosslinked poly β-alanine microspheres obtained above, 2.2 liters of water are added and the mixture is homogenized by stirring. After cooling to a temperature between 5 and 10° C., there is slowly added a cooled solution of sodium borohydride in water (5.2 g of NaBH$_4$ in 600 ml of water cooled to 5° C.). The reaction mixture is maintained between 5 and 1° C. for 5 hours at which point the pH is adjusted to 7 by the addition of acetic acid.

After centrifuging the mixture and dispersing the solid residue in 450 ml of water, the dispersion is submitted to a continuous washing with 5 liters of water (washing in an "AMICON" type cell equipped with a 0.2 μm DIAPOR filter, pressure -200,000 Pa, with stirring during the whole of the washing). The hydrated microspheres are then dried by lyophilization. The absence of coloration in the presence of a Schiff reagent permits to conclude that the residual aldehyde functions have been reduced. After analysis, the diameter of the microspheres is identical to the starting microspheres.

D—Impregnation of the Crosslinked Poly β-alanine Microspheres

1. There are introduced into a container, fitted with a powerful and slow stirrer, 100 g of crosslinked poly β-alanine microspheres such as those obtained above and 300 g of glycerol. The initially pastey mixture progressively takes the form of a gel which is then disaggregated by stirring until a powder having a homogeneous appearance is produced after two hours of malaxing, at ambient temperature and in the absence of atmospheric humidity.

2. There are introduced into a gel composed of 5 g of crosslinked poly β-alanine, prepared as mentioned above, and 50 g of water, 15 g of glycerol. After homogenization the mixture is concentrated in a rotating evaporator at 50°-60° C. under 2700 Pa until a constant weight is obtained.

3. There are introduced into a container, fitted with a powerful and slow stirrer, 100 g of crosslinked poly β-alanine microspheres such as obtained above and 150 g of about 70 weight percent solution of sorbitol. After mixing there is noted the formation of a pasty mixture which is then disaggregated, until a homogeneous powder is produced, by stirring at ambient temperature and in the absence of atmospheric humidity.

4. There are introduced into a container fitted with a powerful stirrer, 100g of crosslinked poly β-alanine microspheres, obtained above, and 50g of Polyethylene Glycol 300, sold by Hoechst, the mixture being provided in the form of a paste which is disaggregated on stirring until the attainment of a homogeneous powder, at ambient temperature and in the absence of humidity.

5. In accordance with the same operating procedures above, there are obtained crosslinked poly β-alanine microspheres impregnated with Polyglycerine 500, sold by Sakamoto Yakuhin (50g of polyglycerine 500 per 100g of crosslinked poly β-alanine microspheres.

In accordance with these same operating procedures, it is possible to obtain crosslinked poly β-alanine microspheres impregnated with other polyhydric alcohols and at various weights by varying the amount of the impregnating polyhydric alcohol in the limits between 10 and 600 weight percent of polyhydric alcohol relative to the weight of the crosslinked poly β-alanine.

EXAMPLES OF MAKEUP COMPOSITIONS

EXAMPLE 1

Eyelid Makeup

| | |
|---|---|
| Crosslinked poly β-alanine microspheres impregnated with glycerol at 300%, in accordance with Example D-1 | 5% |
| Pigments | 30% |
| Mica-titanium | 50% |
| Liquid lanolin | 5% |
| Petrolatum oil | 4.8% |
| Propyl parahydroxybenzoate | 0.2% |
| Talc, sufficient amount for | 100% |

EXAMPLE 2

Cheek Makeup

| | |
|---|---|
| Crosslinked poly β-alanine microspheres impregnated with sorbitol at 100% in accordance with Example D-3 | 4% |
| Magnesium carbonate | 1% |
| Starch | 10% |
| Zinc stearate | 2% |
| Mica-titanium | 2% |
| Liquid lanolin | 2% |
| Petrolatum oil | 2.9% |
| Propyl parahydroxy benzoate | 0.1% |
| Pigments | 30% |
| Perfume | 1% |
| Talc, sufficient amount for | 100% |

EXAMPLE 3

Lip Rouge

| | |
|---|---|
| Crosslinked poly β-alanine microspheres impregnated with glycerol at 300%, in accordance with Example D-1 | 20 g |
| Ozokerite | 12 g |
| Microcrystalline wax | 4 g |
| Candellila wax | 6 g |
| Jojoba oil | 5 g |
| Ricin oil | 1 g |
| Liquid lanolin | 15 g |
| Acetylated lanolin | 8 g |
| Petrolatum oil | 9 g |
| Talc | 3 g |
| Mica-titanium | 7 g |
| D and C Red 7, calcium lake | 4.2 g |
| D and C Red 6, barium lake | 2.3 g |
| FDC Yellow 5 | 0.8 g |
| Titanium dioxide | 2.5 g |
| Butylhydroxy toluene | 0.2 g |
| Perfume, sufficient amount | |

EXAMPLE 4

Eyelid Makeup

| | |
|---|---|
| Crosslinked poly β-alanine microspheres impregnated with sorbitol at 100%, in accordance with Example D-3 | 3 g |
| Candellila wax | 9 g |
| Microcrystalline wax | 8 g |
| Cocoa butter | 13 g |
| Isopropyl myristate | 34.9 g |
| Talc | 7 g |
| Mica-titanium | 10 g |
| Titanium dioxide | 10 g |
| Iron oxide | 5 g |
| Butylhydroxy toluene | 0.1 g |

EXAMPLE 5

Cheek Makeup

| | |
|---|---|
| Crosslinked poly β-alanine microspheres impregnated with glycerol at 300%, in accordance with Example D-2 | 2 g |
| Paraffin oil | 50.65 g |
| Petrolatum | 10 g |
| Carnauba wax | 5 g |
| Ozokerite | 5 g |
| Mica-titanium | 10 g |
| Titanium dioxide | 5 g |
| D and C Red 7 | 0.2 g |
| Iron oxides | 2 g |
| Propyl parahydroxy benzoate | 0.1 g |
| Butylhydroxy toluene | 0.05 g |

EXAMPLE 6

Eyelid Makeup

| | |
|---|---|
| Crosslinked poly β-alanine microspheres impregnated with Polyethylene Glycol 300 at 50%, in accordance with Example D-4 | 6% |
| Pigments | 5% |
| Mica titanium | 50% |
| Liquid lanolin | 7% |
| Petrolatum oil | 5.8% |
| Propyl parahydroxybenzoate | 0.2% |
| Talc | 26% |

EXAMPLE 7

Eyelid Makeup

| | |
|---|---|
| Crosslinked poly β-alanine microspheres impregnated with Polyglycerine 500 at 50%, in accordance with Example D-5 | 6% |
| Mica titanium | 48% |
| Pigments | 24% |
| Talc | 7% |
| Liquid lanolin | 7.5% |
| Petrolatum oil | 7.3% |
| Propyl parahydroxybenzoate | 0.2% |

What is claimed is:

1. In an anhydrous cosmetic makeup composition for the skin and lips, the improvement comprising from 0.1 to 60 weight percent based on the total weight of said composition of crosslinked poly β-alanine microspheres having a diameter ranging from 0.1 to 7 μm and impregnated with between 10 and 600 weight percent of a polyhydric alcohol so as to improve the stability and emollient properties of said composition said polyhydric alcohol being selected from the group consisting of an alcohol having from 2 to 8 carbon atoms and from 2 to 6 hydroxy functions and a polyether alcohol having an average molecular weight between 150 and 600.

2. The composition of claim 1 wherein said polyhydric alcohol is ethylene glycol, glycerol, 1,2-propanediol, diglycerine, erythritol, arabitol, adonitol, sorbitol or dulcitol.

3. The composition of claim 1 wherein said polyether alcohol is polyethylene glycol or polyglycerine.

4. The composition of claim 1 wherein said microspheres are present in an amount ranging from 0.5 to 40 weight percent based on the total weight of said composition.

5. The composition of claim 1 in the form of a powder, compacted or not and comprising
- 0.1 to 60 weight percent of crosslinked poly β-alanine microspheres impregnated with polyhydric alcohol,
- 0 to 20 weight percent of a fatty body comprising an oil or a mixture of at least one oil and at least one wax,
- 1 to 70 weight percent of a colored pigment and
- 5 to 90 weight percent of a mineral or organic charge comprising talc or starch.

6. The composition of claim 1 in the form of a fatty product comprising
- 0.1 to 60 weight percent of crosslinked poly β-alanine microspheres impregnated with polyhydric alcohol,
- 5 to 98 weight percent of a fatty body comprising an oil or a mixture of at least one oil and at least one wax,
- 0 to 80 weight percent of a solvent, and
- 1 to 30 weight percent of a colored pigment.

7. The composition of claim 1 in the form of a lip rouge, colored or not, comprising
- 0.1 to 60 weight percent of crosslinked poly β-alanine microspheres impregnated with polyhydric alcohol,
- 20 to 95 weight percent of a fatty body comprising an oil or a mixture of at least one oil and at least one wax,
- 0.2 to 10 weight percent of a mineral or organic charge comprising talc or starch, and
- 0 to 25 weight percent of a colored pigment.

8. The composition of claim 1 which also includes at least one of an antioxidant agent, a perfume or a preservative.

* * * * *